US012324606B2

(12) United States Patent
Pilletere et al.

(10) Patent No.: US 12,324,606 B2
(45) Date of Patent: Jun. 10, 2025

(54) SEAL ASSEMBLIES FOR SURGICAL ACCESS ASSEMBLIES

(71) Applicant: Covidien LP, Mansfield, MA (US)

(72) Inventors: Roy J. Pilletere, North Haven, CT (US); Jason T. Mickus, Avon, CT (US); Nicolette R. Lapierre, Windsor Locks, CT (US); Matthew A. Dinino, Newington, CT (US); Eric L. Brown, Madison, CT (US)

(73) Assignee: Covidien LP, Mansfield, MA (US)

( * ) Notice: Subject to any disclaimer, the term of this patent is extended or adjusted under 35 U.S.C. 154(b) by 1173 days.

(21) Appl. No.: 16/774,206

(22) Filed: Jan. 28, 2020

(65) Prior Publication Data

US 2021/0228233 A1 Jul. 29, 2021

(51) Int. Cl.
*A61B 17/34* (2006.01)
*A61B 17/32* (2006.01)

(52) U.S. Cl.
CPC ...... *A61B 17/3462* (2013.01); *A61B 17/3423* (2013.01); *A61B 17/3498* (2013.01); *A61B 2017/320044* (2013.01)

(58) Field of Classification Search
CPC ........ A61B 17/3462; A61B 2017/3464; A61B 17/3498; A61B 2017/3445; A61B 17/3415

See application file for complete search history.

(56) References Cited

U.S. PATENT DOCUMENTS

| 3,402,710 | A | 9/1968 | Paleschuck |
|---|---|---|---|
| 3,495,586 | A | 2/1970 | Regenbogen |
| 4,016,884 | A | 4/1977 | Kwan-Gett |
| 4,112,932 | A | 9/1978 | Chiulli |
| 4,183,357 | A | 1/1980 | Bentley et al. |
| 4,356,826 | A | 11/1982 | Kubota |
| 4,402,683 | A | 9/1983 | Kopman |
| 4,653,476 | A | 3/1987 | Bonnet |
| 4,737,148 | A | 4/1988 | Blake |
| 4,863,430 | A | 9/1989 | Klyce et al. |
| 4,863,438 | A | 9/1989 | Gauderer et al. |

(Continued)

FOREIGN PATENT DOCUMENTS

| CA | 2702419 A1 | 11/2010 |
|---|---|---|
| EP | 0226026 A2 | 6/1987 |

(Continued)

OTHER PUBLICATIONS

European Search Report dated Jun. 29, 2021, corresponding to counterpart European Application No. 21153953.1; 9 pages.

(Continued)

*Primary Examiner* — Brigid K Byrd
(74) *Attorney, Agent, or Firm* — Draft Masters IP, LLC

(57) ABSTRACT

Access assemblies include an instrument valve housing and a valve assembly disposed within the cavity of the instrument valve housing. The valve assembly includes a guard assembly, and a seal assembly disposed distal of the guard assembly. The seal assembly includes a support member including a ring portion and a seal portion disposed within the ring portion. The seal assembly further includes a plurality of seal sections extending from the ring portion of the support member. The support member and the plurality of seal sections are integrally formed.

20 Claims, 11 Drawing Sheets

(56) References Cited

U.S. PATENT DOCUMENTS

| | | |
|---|---|---|
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,628,732 A * | 5/1997 | Antoon, Jr. ........ A61B 17/3462 604/256 |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |

(56) References Cited

U.S. PATENT DOCUMENTS

| | | |
|---|---|---|
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,481,795 B2 * | 1/2009 | Thompson ......... A61B 17/3462 604/167.03 |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,128,599 B2 * | 3/2012 | Okoniewski .......... A61M 29/085 604/167.06 |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |

(56) References Cited

U.S. PATENT DOCUMENTS

| | | |
|---|---|---|
| 10,568,660 B2 | 2/2020 | Zhou |
| 10,653,449 B2 | 5/2020 | Main et al. |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0185453 A1* | 8/2007 | Michael ............ A61B 17/3462 604/164.01 |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0005740 A1* | 1/2009 | Smith ............ A61B 17/3474 604/256 |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2009/0326463 A1* | 12/2009 | Ross ............ A61B 17/3423 604/167.01 |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |

(56) References Cited

U.S. PATENT DOCUMENTS

| | | |
|---|---|---|
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0196322 A1 | 7/2015 | Sauter |
| 2015/0216560 A1* | 8/2015 | Holsten .............. A61B 17/3423 600/204 |
| 2018/0021063 A1* | 1/2018 | Main .................. A61B 17/34 604/167.01 |
| 2018/0116691 A1* | 5/2018 | Reid .................. A61B 34/74 |
| 2019/0059938 A1 | 2/2019 | Holsten |
| 2019/0059944 A1 | 2/2019 | Holsten |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| EP | 3242615 A1 | 11/2017 |
| EP | 3730183 A1 | 10/2020 |
| EP | 3753513 A1 | 12/2020 |
| GB | 2469083 | 4/2009 |
| JP | 2018504197 A | 2/2018 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |
| WO | 2012131746 A1 | 10/2012 |
| WO | 2014052532 A1 | 4/2014 |
| WO | 2016110720 A1 | 7/2016 |

OTHER PUBLICATIONS

Japanese Patent Application No. 2021-000731, Office Action dated Sep. 4, 2024, 9 pgs.

* cited by examiner

SEAL ASSEMBLIES FOR SURGICAL ACCESS ASSEMBLIES

FIELD

The present disclosure relates to surgical access assemblies for minimally invasive surgery. More particularly, the present disclosure relates to seal assemblies for surgical access assemblies.

BACKGROUND

In order to facilitate minimally invasive surgery, a working space must be created at the desired surgical site. An insufflation fluid, typically $CO_2$, is introduced into the abdomen of the patient to create an inflated state called a pneumoperitoneum. Access assemblies are utilized to allow the introduction of surgical instrumentation and endoscopes (or other visualization tools). These access assemblies maintain the pressure for the pneumoperitoneum, as they have one or more seals that adapt to the surgical instrumentation. Typically, a "zero-seal" in the access assembly seals the access assembly in the absence of a surgical instrument in the access assembly, and an instrument seal seals around a surgical instrument that has been inserted through the access assembly.

The breadth of surgical instrumentation on the market today requires a robust seal capable of adjusting to multiple sizes and withstanding multiple insertions of surgical instrumentation. Some of the instrumentation can include sharp edges that can tear or otherwise damage seals. Therefore, it would be beneficial to have an access assembly with improved seal durability.

SUMMARY

An access assembly includes an instrument valve housing including upper, lower, and inner housing sections and defining a cavity. A valve assembly is disposed within the cavity of the instrument valve housing. The valve assembly includes a guard assembly, and a seal assembly disposed distally of the guard assembly. The seal assembly includes a support member and a plurality of seal sections connected to the support member. The support member includes a ring portion and a seal portion disposed within the ring portion. The support member and the plurality of seal sections are integrally formed.

In embodiments, the seal assembly includes first, second, third, fourth seal, fifth, and sixth seal sections. The ring portion may be hexagonal. Each seal section of the plurality of seal sections may include a substantially wing shape. An inner edge of each seal section of the plurality of seal sections may be tapered.

In some embodiments, each seal section of the plurality of seal sections is connected to the ring portion by a living hinge. Each seal section of the plurality of seal sections may overlap two adjacent seal sections of the plurality of seal sections in a clockwise direction. Each seal section of the plurality of seal sections may overlap two adjacent seal sections of the plurality of seal sections in a counter-clockwise direction.

The access assembly may further include a retainer assembly including an upper retainer member, a lower retainer member, and a plurality of pins extending from one of the upper or lower retainer members. Each pin of the plurality of pins may be received through an opening in three seal sections of the plurality seal sections and through an opening in the ring portion of the support member.

Also provided is a valve assembly including a guard assembly, and a seal assembly disposed distal of the guard assembly. The seal assembly includes a support member and a plurality of seal sections connected to the support member. The support member includes a ring portion and a seal portion disposed within the ring portion. The support member and the plurality of seal sections are integrally formed.

In embodiments, the seal assembly includes first, second, third, fourth seal, fifth, and sixth seal sections. The ring portion may be hexagonal. Each seal section of the plurality of seal sections may include a substantially wing shape. An inner edge of each seal section of the plurality of seal sections may be tapered.

In some embodiments, each seal section of the plurality of seal sections is connected to the ring portion by a living hinge. Each seal section of the plurality of seal sections may overlap two adjacent seal sections of the plurality of seal sections in a clockwise direction. Each seal section of the plurality of seal sections may overlap two adjacent seal sections of the plurality of seal sections in a counter-clockwise direction.

The access assembly may further include a retainer assembly including an upper retainer member, a lower retainer member, and a plurality of pins extending from one of the upper or lower retainer members. Each pin of the plurality of pins may be received through an opening in three seal sections of the plurality seal sections and through an opening in the ring portion of the support member.

In addition, provided is a seal assembly including a support member having a ring portion and a seal portion disposed within the ring portion, and a plurality of seal sections extending from the ring portion of the support member. The support member and the plurality of seal sections are integrally formed.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
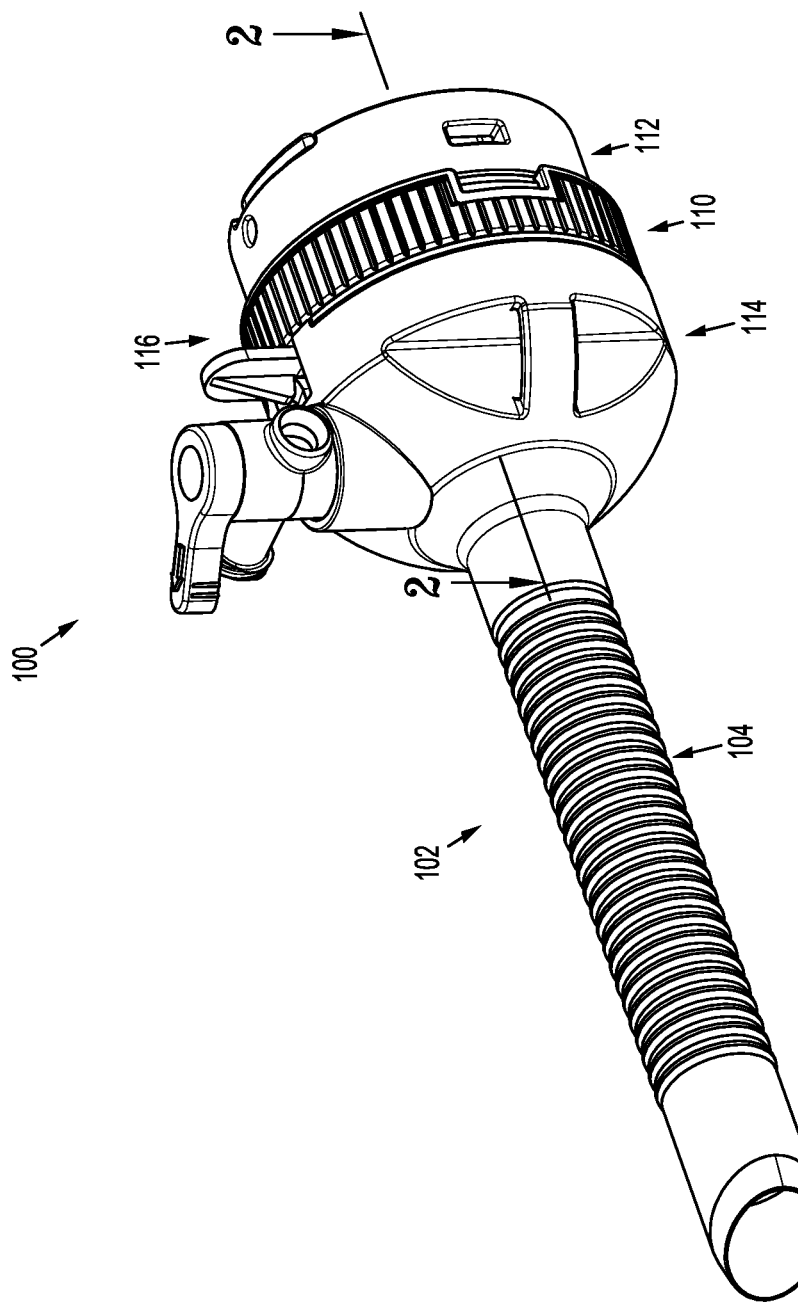
FIG. 1 is a side perspective view of a surgical access assembly according to an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Surgical access assemblies with obturators are employed during minimally invasive surgery, e.g., laparoscopic surgery, and provide for the sealed access of surgical instruments into an insufflated body cavity, such as the abdominal cavity. The surgical access assemblies of the present disclosure include an instrument valve housing mounted on a cannula tube, and include an obturator (not shown) inserted through the valve housing and cannula. The obturator can have a blunt distal end, or a bladed or non-bladed penetrating distal end and can be used to incise the abdominal wall so that the surgical access assembly can be introduced into the abdomen. The handle of the obturator can engage or selectively lock into the instrument valve housing of the surgical access assembly.

Surgical access assemblies are employed to tunnel through an anatomical structure, e.g., the abdominal wall, either by making a new passage through the anatomical structure or by passing through an existing opening through the anatomical structure. Once the surgical access assembly with the obturator has tunneled through the anatomical structure, the obturator is removed, leaving the surgical access assembly in place. The instrument valve housing of the surgical access assembly includes valves that prevent the escape of insufflation fluid from the body cavity, while also allowing surgical instruments to be inserted into the body cavity.

In various embodiments, a bladeless optical trocar obturator may be provided that permits separation of tissue planes in a surgical procedure and visualization of body tissue fibers as they are being separated, thereby permitting a controlled traversal across a body wall. In other embodiments, the trocar obturator may be bladeless without being optical, e.g., without providing contemporaneous visualization thereof through the distal tip of an obturator. The bladeless obturator may be provided for the blunt dissection of the abdominal lining during a surgical procedure.

Various trocar obturators suitable for use with the surgical access assembly of the present disclosure are known and include, for example, bladed, bladeless, blunt, optical, and non-optical. For a detailed description of the structure and function of exemplary trocar assemblies, including exemplar trocar obturators and exemplar cannulas, please refer to PCT Publication No. WO 2016/186905 ("the '905 publication"), the content of which is hereby incorporated by reference herein in its entirety.

With initial reference now to FIG. 1, a surgical access assembly according to aspects of the present disclosure is shown generally as surgical access assembly 100. The surgical access assembly 100 includes a cannula 102 and an instrument valve housing 110 secured to the cannula 102. For a detailed description of an exemplary surgical access assembly, please refer to the '905 publication.

Figure 2:
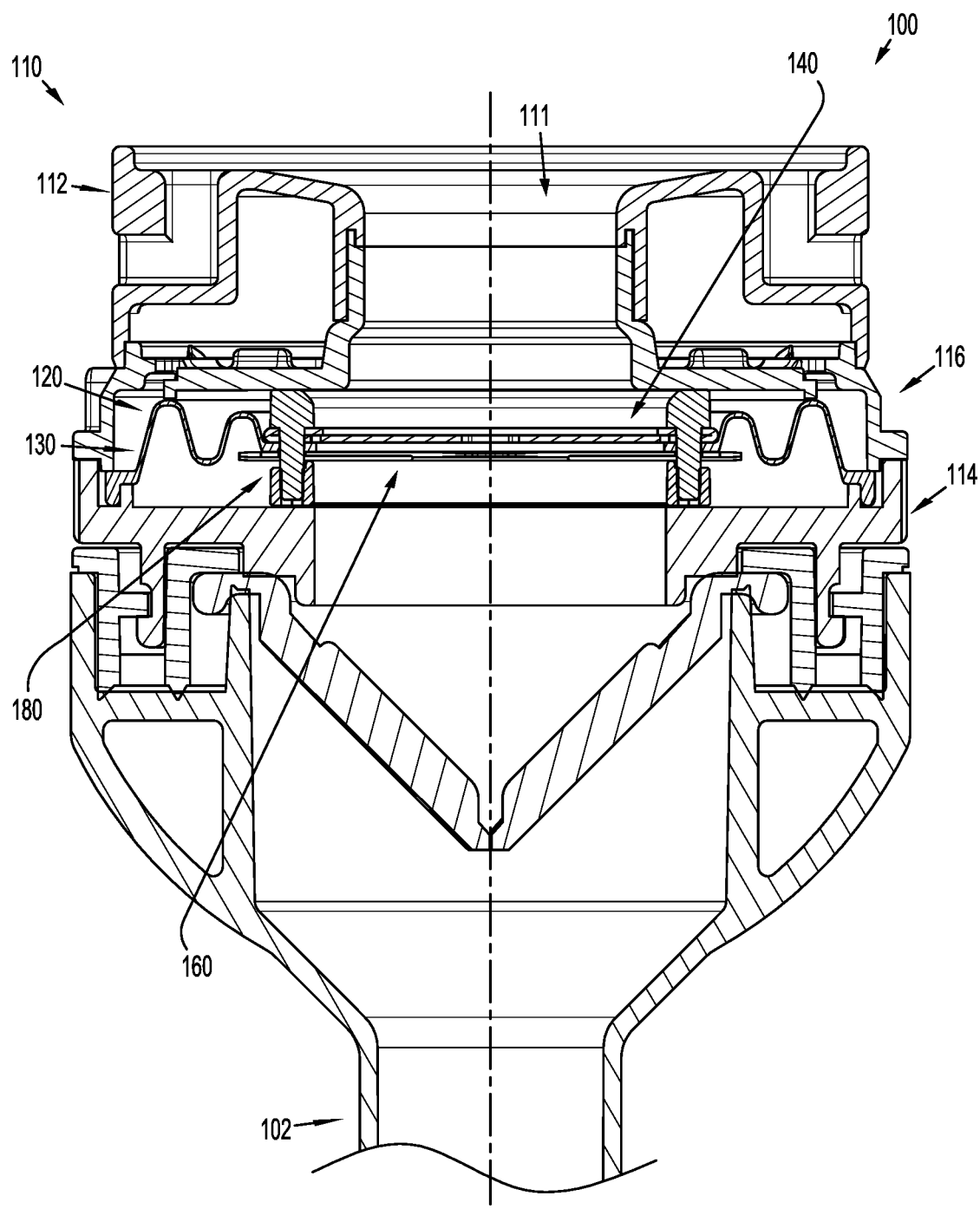
FIG. 2 a side cross-sectional view of the surgical access assembly shown in FIG. 1 taken along section line 2-2.

With reference to FIG. 2, the instrument valve housing 110 of the surgical access assembly 100 includes an upper housing section 112, a lower housing section 114, and an inner housing section 116. The upper, lower, and inner housing sections 112, 114, 116 are configured to support a valve assembly 120 on a proximal end of the cannula 102. More particularly, the inner housing section 116 is secured between the upper and lower housing sections 112, 114, and the valve assembly 120 is received between the inner and lower housing sections 116, 114. The upper and lower housing sections 112, 114 of the instrument valve housing 110 may be selectively attachable to, and detachable from, the inner housing section 116. The lower housing section 114 may be releasably or permanently attached to a cannula tube 104 (FIG. 1) of the cannula 102. In embodiments, either or both of the upper and lower housing sections 112, 114 of the instrument valve housing 110 may include knurls, indentations, tabs, or be otherwise configured to facilitate engagement by a clinician.

The surgical access assembly 100 may also include features for the stabilization of the surgical access assembly. For example, the distal end of the cannula tube 104 may carry a balloon anchor or another expandable member that engages the abdomen from the interior side. For example, see U.S. Pat. No. 7,300,448, the entire disclosure of which is hereby incorporated by reference herein. A feature on the opposite side of the abdominal wall may be used to further stabilize the surgical access assembly, such as adhesive tabs or adjustable foam collars.

The upper, lower, and inner housing sections 112, 114, 116 of the instrument valve housing 110 define a longitudinal passage 111 for receipt of a surgical instrument (not shown). The valve assembly 120 is supported within the instrument valve housing 110 to provide sealed passage of the surgical instrument (not shown) through the surgical access assembly 100.

Figure 3:
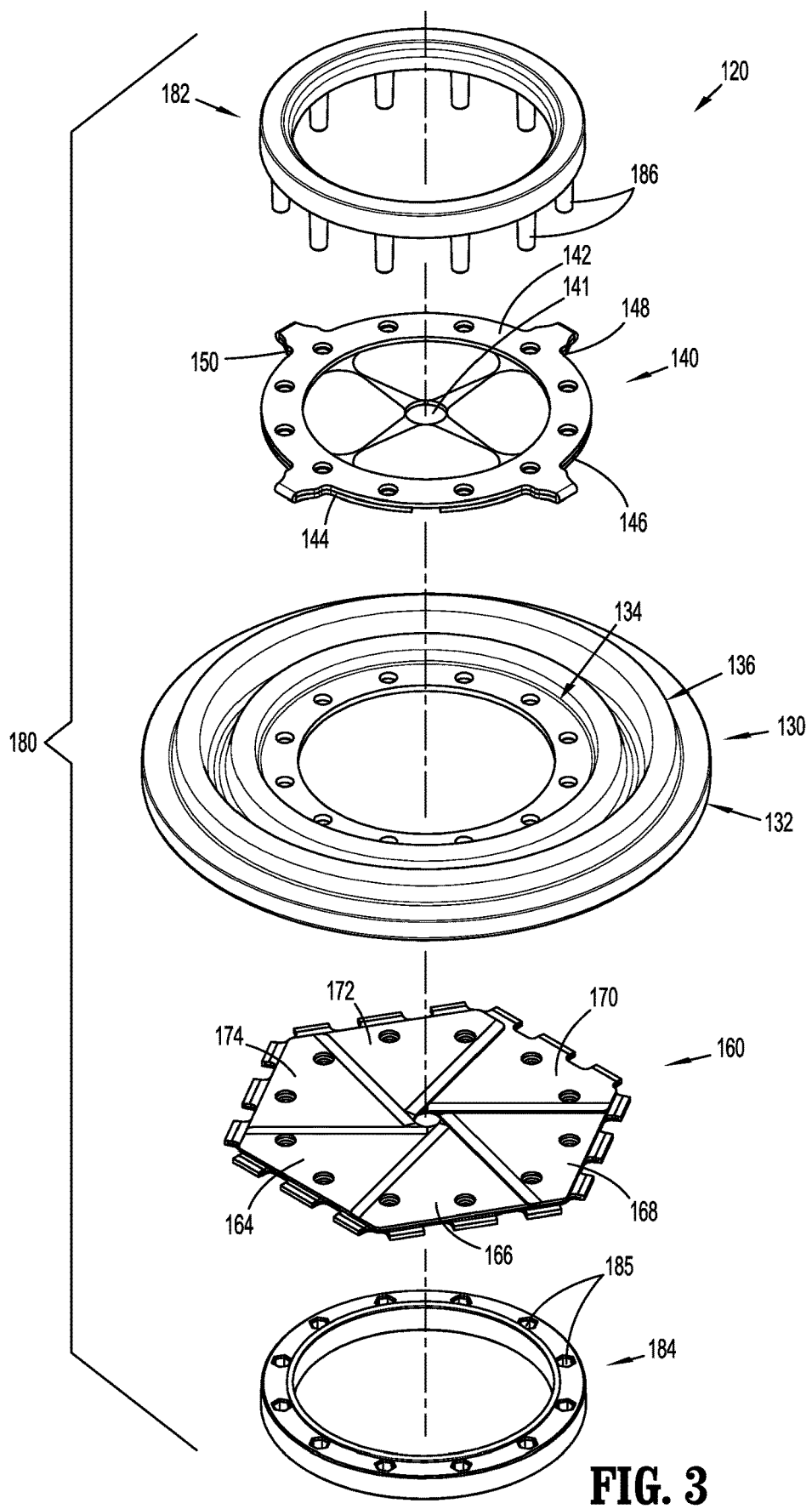
FIG. 3 is an exploded perspective view of a valve assembly, with parts separated, including a centering mechanism, a guard assembly, a seal assembly, and a retainer assembly.

With particular reference to FIGS. 2 and 3, the valve assembly 120 supported in the instrument valve housing 110 (FIG. 2) includes a centering mechanism 130, a guard assembly 140, a seal assembly 160, and a retainer assembly 180. The centering mechanism 130 of the valve assembly 120 permits radial movement of the valve assembly 120 relative to the instrument valve housing 110 when a surgical instrument is received through the valve assembly 120, and returns the valve assembly 120 to a generally centered position once the surgical instrument is withdrawn from within the instrument valve housing 110. The guard assembly 140 protects the seal assembly 160 during insertion and withdrawal of a surgical instrument through the seal assembly 160. The seal assembly 160 provides sealed passage of the surgical instrument through the instrument valve housing 110. The retainer assembly 180 maintains the centering mechanism 130, the guard assembly 140, and the seal assembly 160 in an aligned relationship with one another.

With continued reference to FIGS. 2 and 3, as noted above, the centering mechanism 130 of the valve assembly 120 is configured to maintain the valve assembly 120 centered within the instrument valve housing 110 (FIG. 2) in the absence of a surgical instrument passing through the valve assembly 120. In embodiments, and as shown, the centering mechanism 130 includes an outer annular ring 132, an inner annular ring 134, and a bellows 136 disposed between the outer annular ring 132 and the inner annular ring 134. As shown in FIG. 2, the outer annular ring 132 is received between the inner housing section 116 and the lower housing section 114 to retain the centering mechanism 130 within the instrument valve housing 110. The inner annular ring 134 supports the guard assembly 140. For a detailed description of the structure and function of an exemplary centering mechanism, please refer to U.S. Pat. No. 6,702,787, the content of which is incorporated herein by reference in its entirety.

Although shown including the centering mechanism 130 having bellows 136, the valve assembly 120 may include alternative centering mechanisms. For example, the centering mechanism may include an annular base and a plurality of spokes extending from the base, as described in U.S. Pat. App. Pub. No. 2015/0025477 ("the '477 publication"), the content of which is incorporated herein by reference in its entirety. It is envisioned that the centering mechanism may include multiple sets of spokes, as disclosed in the '477 publication.

With continued reference to FIGS. 2 and 3, the guard assembly 140 of the valve assembly 120 is configured to protect the seal assembly 160 as a surgical instrument (not shown) passes through the instrument valve housing 110 (FIG. 2). The guard assembly 140 includes a ring portion 142 and first, second, third, and fourth petals 144, 146, 148, 150. The first, second, third, and fourth petals 144, 146, 148, 150 define an opening 141 therebetween to facilitate scaled passage of a surgical instrument (not shown) through the guard assembly 140. Although shown including four (4) petals, it is envisioned that the guard assembly may include any suitable number of petals, and the petals may include flap portions of any size or configuration. For detailed description of the structure and function of other exemplary guard assemblies, please refer to U.S. Pat. Nos. 5,895,377 and 6,569,120 ("the '377 and '120 patents") and U.S. patent application Ser. Nos. 16/394,043 and 16/238,823, the entire disclosures of which are incorporated herein by reference in their entirety.

Figure 4:
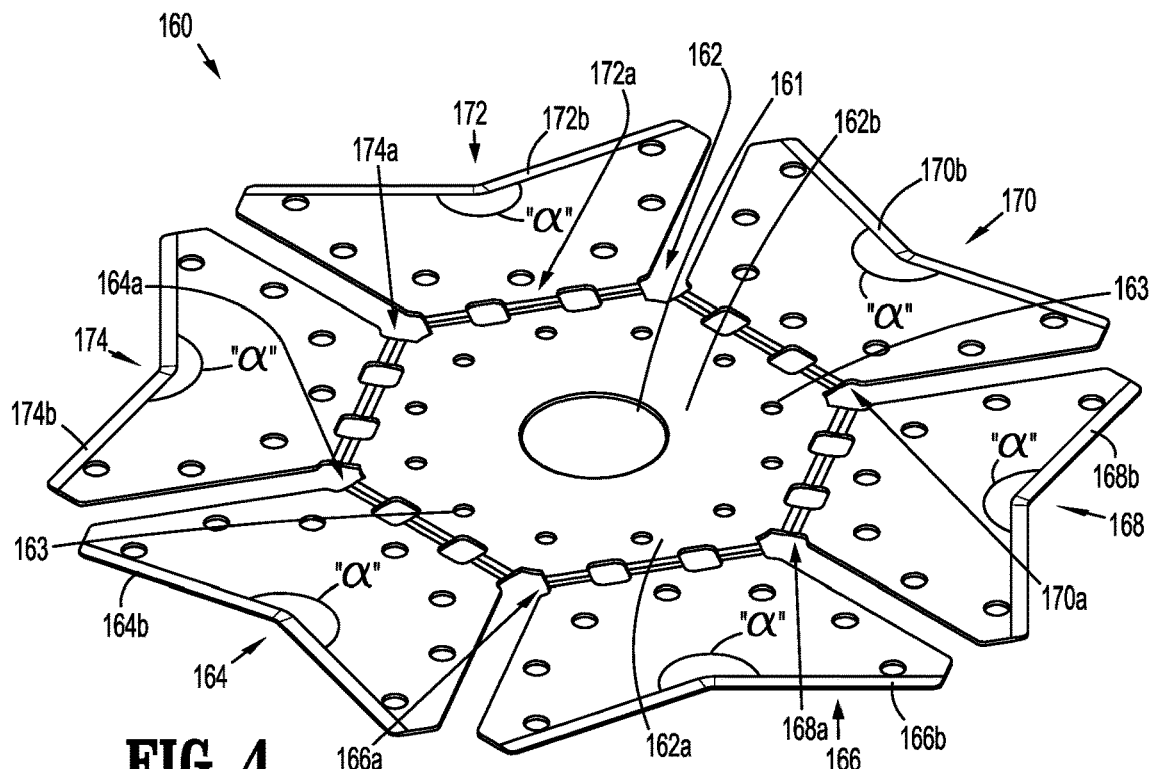
FIG. 4 is a top perspective view of the seal assembly shown in FIG. 3, in an initial or unfolded condition.
Figure 5:
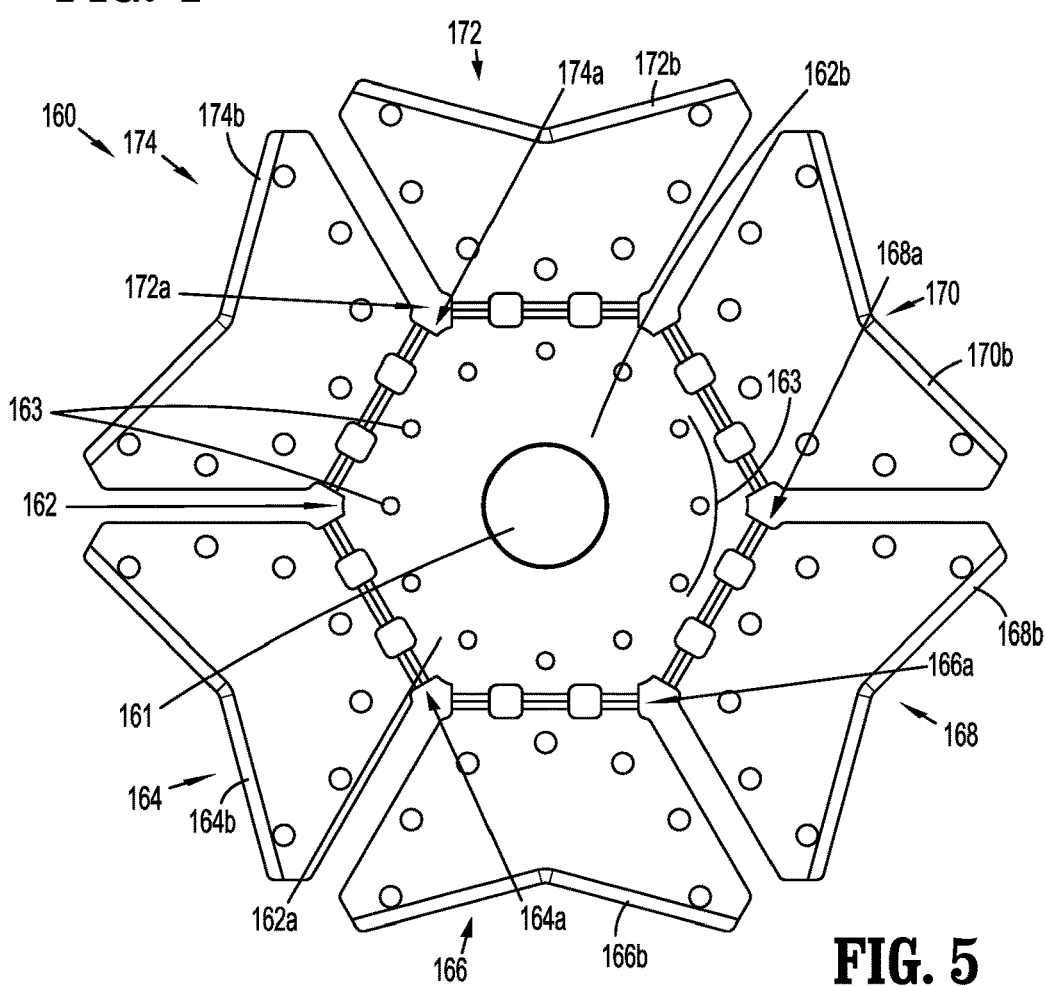
FIG. 5 is a top plan view of the seal assembly shown in FIG. 4, in the initial or unfolded condition.
Figure 6:
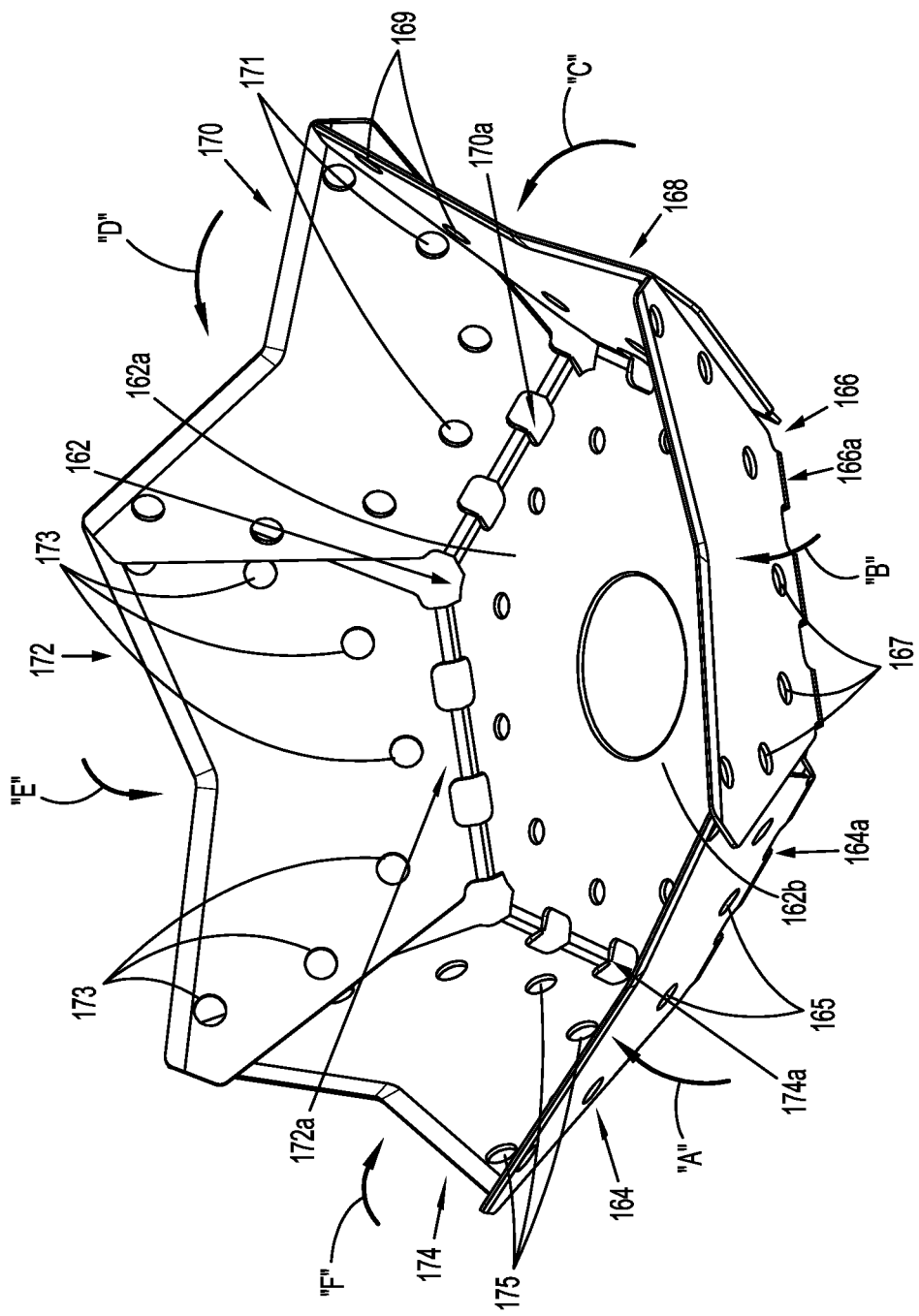
FIG. 6 is a top perspective view of the seal assembly shown in FIGS. 3 and 4, in a partially folded condition.

Referring to FIGS. 4-6, the seal assembly 160 of the valve assembly 120 is configured to provide a seal around an outer surface of a surgical instrument passing through the instrument valve housing 110 (FIG. 1). In embodiments, and as shown, the seal assembly 160 forms a flat seal body; however, it is envisioned that the aspects of the present disclosure may be modified for use with a conical seal body.

The seal assembly 160 includes a support member 162, and first, second, third, fourth, fifth, and sixth seal sections 164, 166, 168, 170, 172, 174 secured to the support member 162 by respective connector portions 164a, 166a, 168a, 170a, 172a, 174a. The connector portions 164a, 166a, 168a, 170a, 172a, 174a may include one or more living hinges, as shown, or be otherwise configured to permit folding of the respective first, second, third, fourth, fifth, and sixth seal sections 164, 166, 168, 170, 172, 174 relative to the support member 162.

In embodiments, the support member 162 and the first, second, third, fourth, fifth, and sixth seal sections 164, 166, 168, 170, 172, 174 of the seal assembly 160 are formed of the same material, including, for example, polyurethane, polyisoprenes, or silicone elastomers. Alternatively, the support member 162, and the first, second, third, fourth, fifth, and sixth seal sections 164, 166, 168, 170, 172, 174 may be formed of different materials. In embodiments, the support member 162 and/or the first, second, third, fourth, fifth, and sixth seal sections 164, 166, 168, 170, 172, 174 may include one or more fabric layers.

Figure 7:
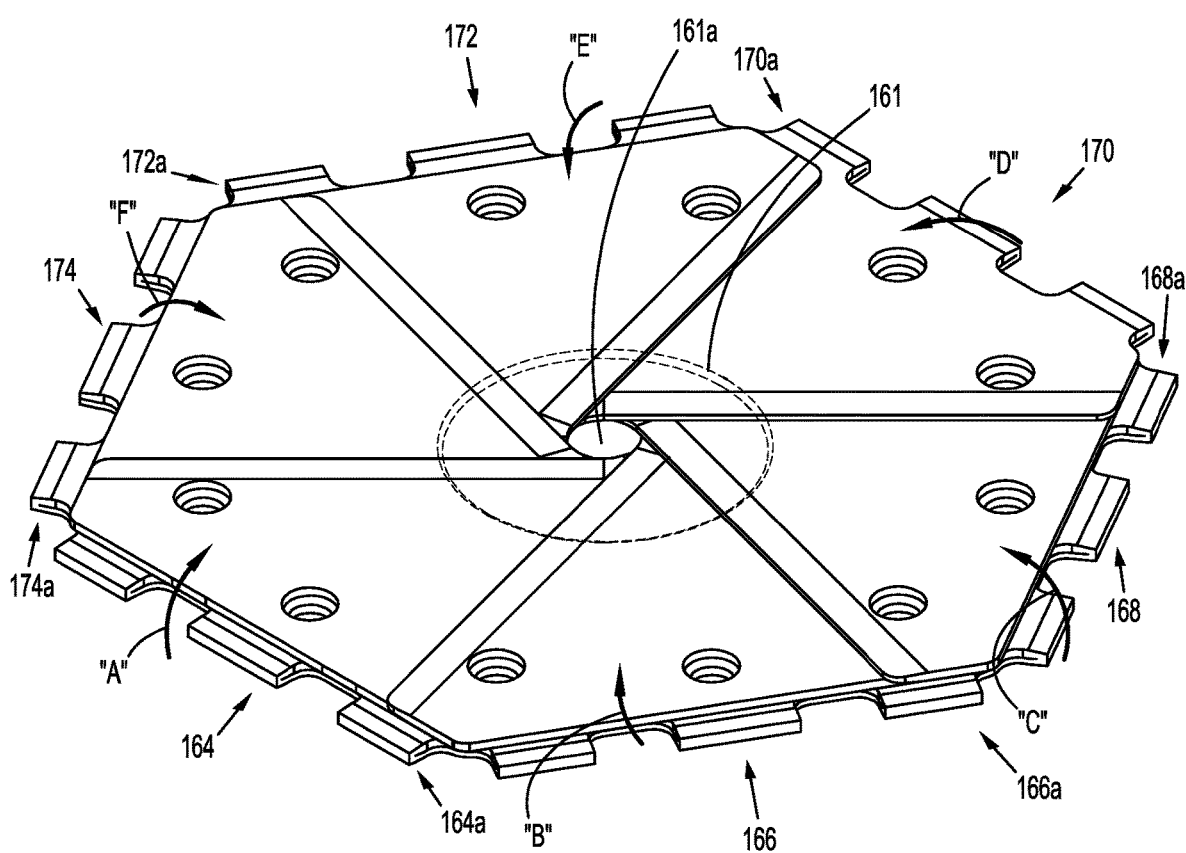
FIG. 7 is a top perspective view of the seal assembly shown in FIGS. 4-6, in a fully folded condition.

As noted above, the first, second, third, fourth, fifth, and sixth seal sections 164, 166, 168, 170, 172, 174 of the seal assembly 160 define a planar configuration when the seal assembly 160 is in the folded condition (FIG. 7). However, the seal assembly 160 may define a conical seal.

The support member 162 of the seal assembly 160 includes a hexagonal body or ring portion 162a and a seal portion 162b supported within the support member 162a. The ring portion 162a and the seal portions 162b may be formed of the same or different materials. The seal portion 162b defines a central opening 161. The support member 162a defines a plurality of openings 163 corresponding to a plurality of pins 186 (FIG. 3) extending from an upper retainer member 182 of the retainer assembly 180. The seal portion 162a provides additional support to the first, second, third, fourth, fifth, and sixth seal sections 164, 166, 168, 170, 172, 174 when the seal assembly 160 is in the folded configuration.

In embodiments, and as shown, the ring portion 162a and the seal portion 162b of the support member 162 are of unitary construction, i.e., monolithic, with the first, second, third, fourth, fifth, and sixth seal sections 164, 166, 168, 170, 172, 174. By incorporating the ring portion 162a with the seal portion 162b of the support member 162 of the seal assembly 160 and forming the first, second, third, fourth, fifth, and sixth seal sections 164, 166, 168, 170, 172, 174 on the ring portion 162a of the support member 162, instead of including a ring portion for the seal portion and a separate ring portion for the first, second, third, fourth, fifth, and sixth seal sections 164, 166, 168, 170, 172, 174, the number of components in the seal assembly 160, and ultimately, the valve assembly 120, is reduced. The incorporation of the seal portion 162b and the first, second, third, fourth, fifth, and sixth seal sections 164, 166, 168, 170, 172, 174 with the same ring portion 162 also reduces assembly time and reduces material costs.

When in the folded condition (FIG. 7), the first, second, third, fourth, fifth, and sixth seal sections 164, 166, 168, 170, 172, 174 of the seal assembly 160 define an opening 161a configured to receive a surgical instrument (not shown) inserted through the valve assembly 120 in a sealed manner. The first, second, third, fourth, fifth, and sixth seal sections 164, 166, 168, 170, 172, 174 form a non-continuous or virtual seal circumference to reduce tearing during insertion, manipulation, and/or withdrawal of a surgical instrument (not shown) through the valve assembly 120.

Each of the first, second, third, fourth, fifth, and sixth seal sections 164, 166, 168, 170, 172, 174 of the seal assembly 160 includes a wing-shaped body. When the seal assembly 160 is in the folded configuration, the first, second, third, fourth, fifth, and sixth seal sections 164, 166, 168, 170, 172, 174 are configured to partially overlap two adjacent seal sections in each of the clockwise and the counter-clockwise directions. More particularly, the first seal section 164 is configured to partially overlap, the sixth and fifth seal sections 174, 172 in the clockwise direction and the second and third seal section 166, 168 in the counter-clockwise direction, the second seal section 164 is configured to partially overlap the first and sixth seal sections 164, 174 in the clockwise direction and the third and fourth seal sections 164, 168 in the counter-clockwise direction, the third seal section 166 is configured to partially overlap the second and first seal sections 166, 164 in the clockwise direction and the fourth and fifth seal section 170, 172 in the counter-clockwise direction, the fourth seal section 170 is configured to partially overlap the third and second seal sections 168, 166 in the clockwise direction and the fifth and sixth seal sections 172, 174 in the counter-clockwise direction, the fifth seal section 172 is configured to partially overlap the fourth and third seal sections 170, 168 in the clockwise direction and the sixth and first seal sections 174, 164 in the counter-clockwise direction, and the sixth seal section 174 is configured to partially overlap the fifth and fourth seal sections 172, 170 in the clockwise direction and the first and second seal sections 164, 166 in the counter clockwise direction.

In embodiments, and as shown, the first, second, third, fourth, fifth, and sixth seal sections 164, 166, 168, 170, 172, 174 are folded such that the first, second, third, fourth, fifth, and sixth seal sections 164, 166, 168, 170, 172, 174 overlap in a sequential pattern in counter-clockwise direction. Alternatively, the first, second, third, fourth, fifth, and sixth seal sections 164, 166, 168, 170, 172, 174 may folded to overlap in a sequential clockwise direction. It is envisioned that the first, second, third, fourth, fifth, and sixth seal sections 164, 166, 168, 170, 172, 174 may instead be folded in opposed pairs, i.e., first and fourth seal sections 164, 170 folded together, second and fifth seal sections, 166, 172 folded together, and third and sixth seal sections 168, 174 folded together, or in any other suitable manner.

An inner edge 164b, 166b, 168b, 170b, 172b, 174b of the respective first, second, third, fourth, fifth, and sixth seal sections 164, 166, 168, 170, 172, 174 of the seal assembly 160 may define a V-shape, as shown, or may extend straight across. In embodiments, the V-shape defines an angle "α" from about one-hundred eighty degrees (180°) to about two-hundred seventy-five degrees (275°)(FIG. 4). The V-shape of the inner edges 164b, 166b, 168b, 170b, 172b 164b facilitates reception of a surgical instrument (not shown) through the seal assembly 160.

Each of the first, second, third, fourth, fifth, and sixth seal sections 164, 166, 168, 170, 172, 174 defines a plurality of openings 165, 167, 169, 171, 173, 175 (FIG. 6) adjacent the respective connector portions 164a, 166a, 168a, 170a, 172a, 174a of each seal section 164, 166, 168, 170, 172, 174, respectively. In embodiments, and as shown, the plurality of openings 165, 167, 169, 171, 173, 175 are arranged such each opening of the plurality of openings 163 in the support member 162 is aligned with an opening of the plurality of openings 165, 167, 169, 171, 173, 175 of the respective first, second, third, fourth, fifth, and sixth seal sections 164, 166, 168, 170, 172, 174 and an opening of the plurality of openings 165, 167, 169, 171, 173, 175 of the two adjacent first, second, third, fourth, fifth, and sixth seal sections 164, 166, 168, 170, 172, 174. In this manner, each pin of the plurality of pins 186 (FIG. 3) of the retainer assembly 180 is received through an opening 163 in the support member 162 and through an opening 165, 167, 169, 171, 173, 175 in three of the six seal sections 164, 166, 168, 170, 172, 174 when the first, second, third, fourth, fifth, and sixth seal sections 164, 166, 168, 170, 172, 174 are secured relative to each other in the assembled configuration. This arrangement ensures the integrity of the seal assembly 160, and more particularly, ensures the positioning of the first, second, third, fourth, fifth, and sixth seal sections 164, 166, 168, 170, 172, 174 relative to each other and the support member 162.

FIGS. 6 and 7 illustrate the method of folding the seal assembly 160. As shown in FIG. 6, each of the first, second, third, fourth, fifth, and sixth seal sections 164, 166, 168, 170, 172, 174 are folded relative to the support member 162 at the respective connector portion 164a. 166a, 168a, 170a, 172a, 174a, as indicated by arrows "A", "B", "C", "D", "E", and "F" respectively. As shown, the first, second, third, fourth, fifth, and sixth seal sections 164, 166, 168, 170, 172, 174 are folded simultaneously, with adjacent seal sections overlapping one another. More particularly, the second seal section 166, overlaps the first seal section 164, the third seal section 168 overlaps the second seal section 166, and so on until the first seal section 164 overlaps the sixth seal section 174. This overlapping or interweaving pattern increases the integrity of the seal assembly 160, i.e., reduces the likelihood of the seal assembly 160 leaking when a surgical instrument is received therethrough. As noted above, alternatively, the seal sections may be folded in any manner, including, with opposed seal sections folded together.

Figure 8:
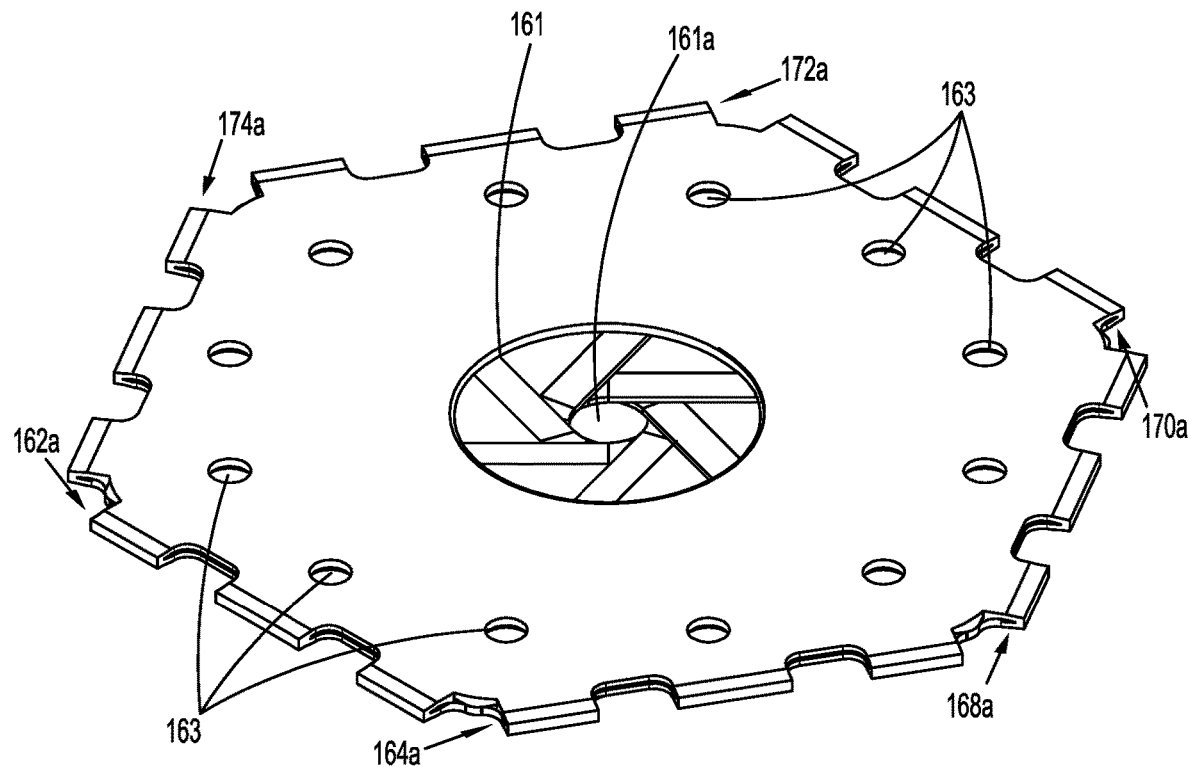
FIG. 8 is a bottom perspective view of the seal assembly shown in FIG. 7.

FIGS. 7 and 8 illustrate the seal assembly 160 in the folded condition. In the folded configuration, the first, second, third, fourth, fifth, and sixth seal sections 164, 166, 168, 170, 172, 174 are disposed adjacent the seal portion 162b of the support member 162.

Figure 9:
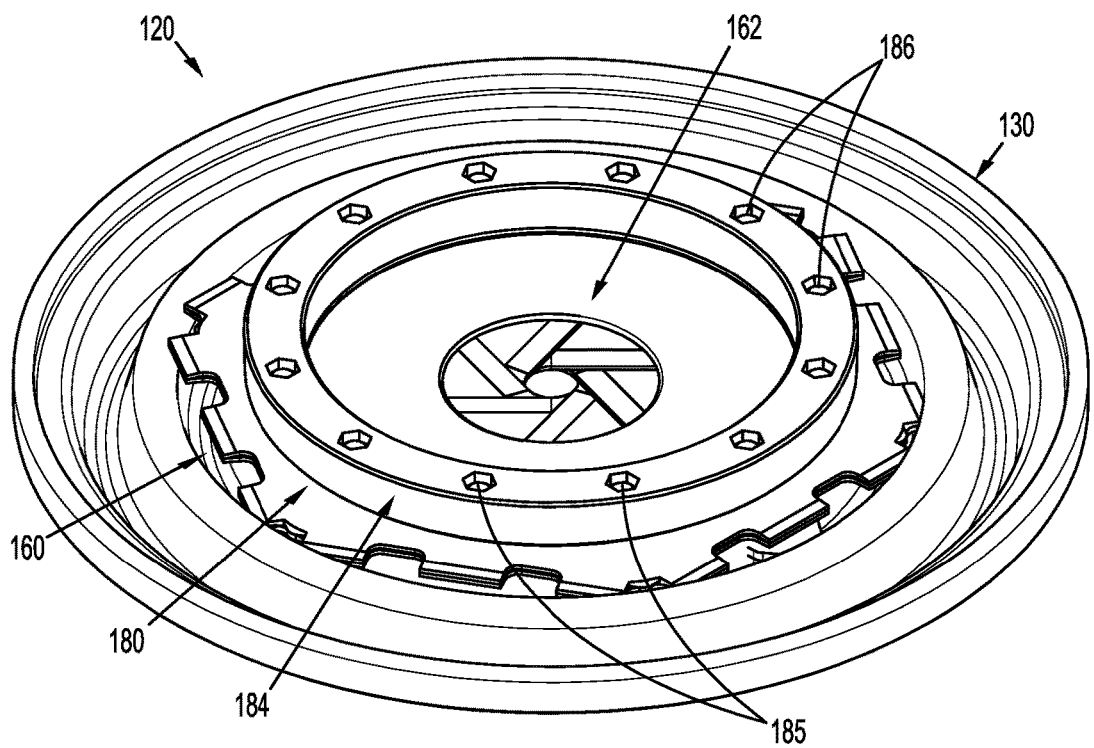
FIG. 9 is a bottom perspective view of the valve assembly shown in FIG. 3, as assembled.
Figure 10:
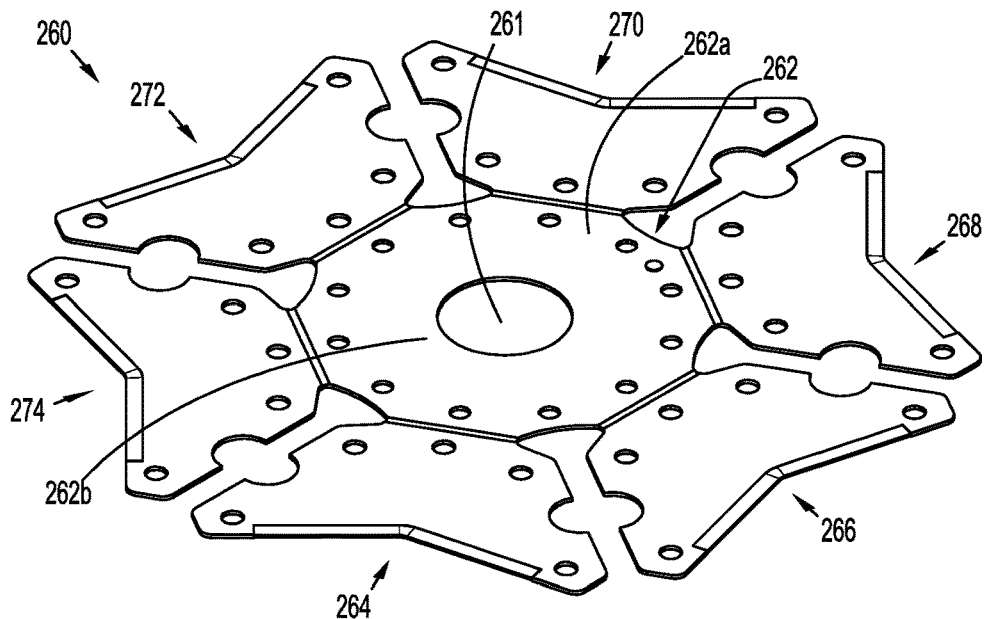
FIG. 10 is a top perspective view of a seal assembly according to another aspect of the disclosure, in an initial or unfolded condition.
Figure 11:
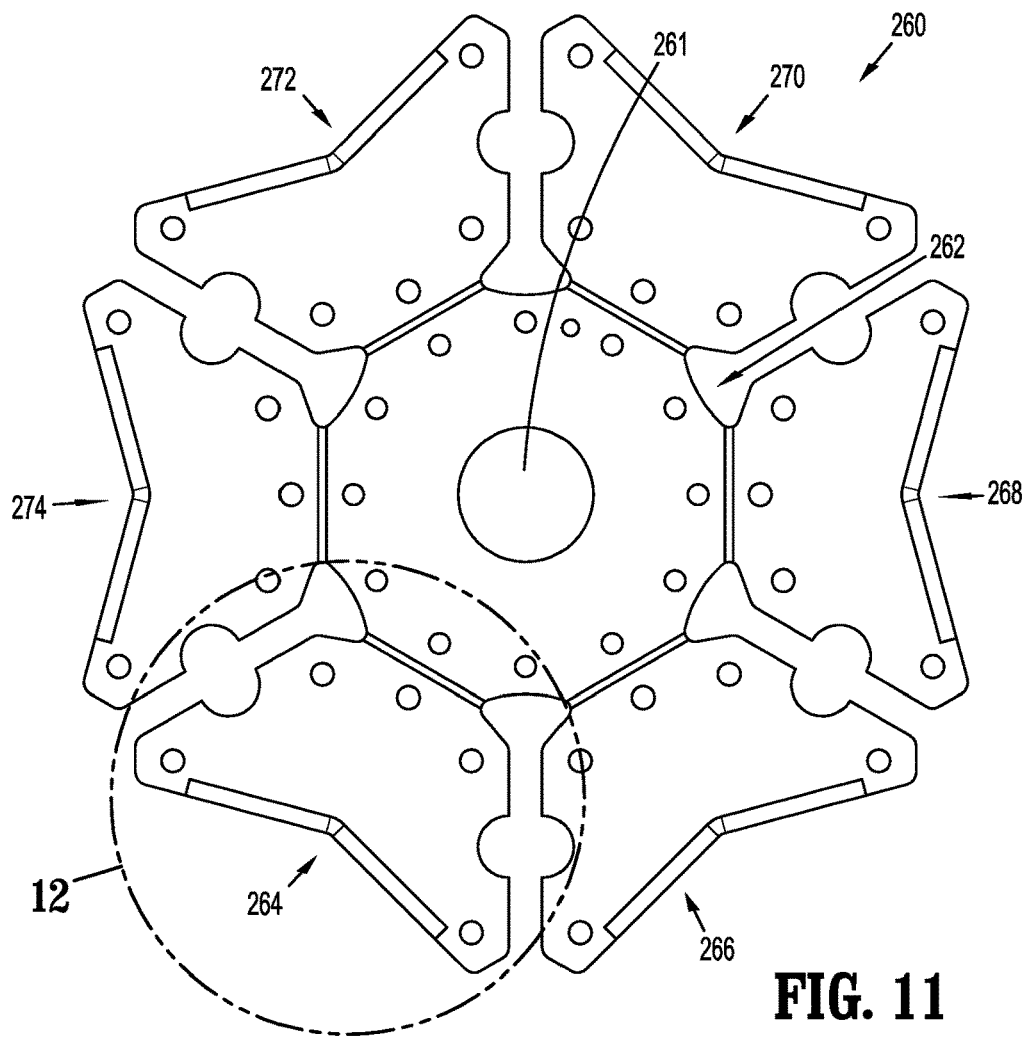
FIG. 11 is a top plan view of the seal assembly shown in FIG. 10, in the initial or unfolded condition.

FIG. 9 illustrates a bottom view of the assembled valve assembly 120. The seal assembly 160 is secured relative to the centering mechanism 130 and the guard assembly 140 (FIG. 3) by retainer assembly 180. More particularly, the plurality of pins 186 extending from the upper retainer member 182 (FIG. 3) of the retainer assembly 180 extend through the guard assembly 140, the centering mechanism 130, and the seal assembly 160, and are secured within openings 185 of the lower retainer member 184. In embodiments, the plurality of pins 186 is welded, glued, adhered, bonded or otherwise secured within the plurality of openings 185 in the lower retainer member 184 to secure the upper retainer member 182 and the lower retainer member 184 together. The lower retainer member 184 may instead, or additionally, include a plurality of pins (not shown) with the upper retainer member 182 defining a plurality of corresponding openings (not shown). Either or both of the upper and lower retainer members 182, 184 may include locking features (not shown) for engaging the plurality of pins 186 and securing the upper retainer member 182 to the lower retainer member 184.

Referring to FIGS. 10-13, a seal assembly according to another aspect of the disclosure is shown generally as seal assembly 260. The seal assembly 260 is substantially similar to the seal assembly 160 described hereinabove, and will only be described in detail with regards to the differences therebetween. The seal assembly 260 is configured to be received within the instrument valve housing 110 (FIG. 1) and provide a seal around an outer surface of a surgical instrument passing through the instrument valve housing 110. As shown, the seal assembly 260 forms a flat seal body; however, it is envisioned that the aspects of the disclosure may be modified for use with a conical seal body.

The seal assembly 260 includes a support member 262, and first, second, third, fourth, fifth, and sixth seal sections 264, 266, 268, 270, 272, 274 secured to the support member 262. In some aspects of the disclosure, the support member 262 and the first, second, third, fourth, fifth, and sixth seal sections 264, 266, 268, 270, 272, 274 of the seal assembly 260 are formed of the same material, including, for example, polyurethane, polyisoprenes, or silicone elastomers. Alternatively, the support member 262, and the first, second, third, fourth, fifth, and sixth seal sections 264, 266, 268, 270, 272, 274 are formed of different materials. In other aspects, the support member 262 and/or the first, second, third, fourth, fifth, and sixth seal sections 264, 266, 268, 270, 272, 274 may include one or more fabric layers.

Figure 14:
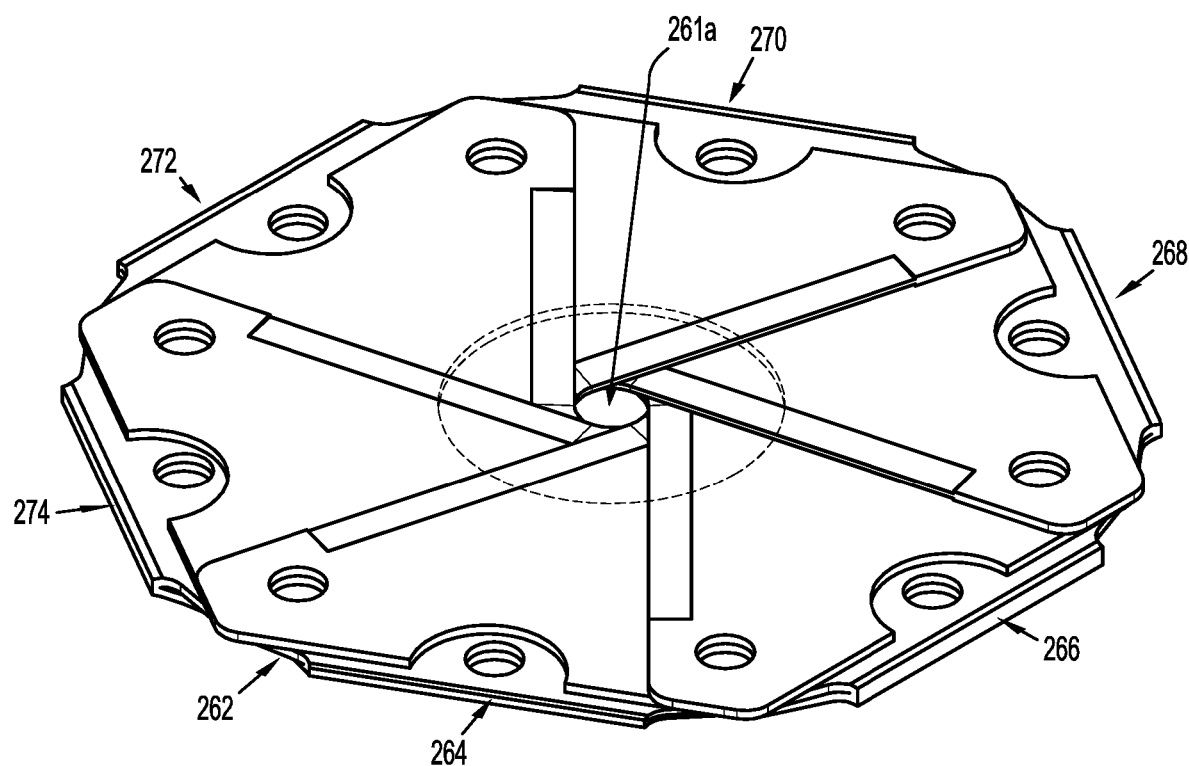
FIG. 14 is a top perspective view of the seal assembly shown in FIGS. 10-13, in a fully folded condition.

As noted above, the first, second, third, fourth, fifth, and sixth seal sections 264, 266, 268, 270, 272, 274 of the seal assembly 260 define a planar configuration when the seal assembly 260 is in the folded condition (FIG. 14). However, the seal assembly 260 may define a conical seal when in the folded condition.

The support member 262 of the seal assembly 260 includes a hexagonal body or ring portion 262a and a seal portion 262b supported within the support member 262a. The ring portion 262a and the seal portions 262b may be formed of the same or different materials. The seal portion 262b defines a central opening 261. The support member 262a defines a plurality of openings 263 (FIG. 12) corresponding to the plurality of pins 186 (FIG. 3) extending from the upper retainer member 182 of the retainer assembly 180. The seal portion 262a provides additional support to the first, second, third, fourth, fifth, and sixth seal sections 264, 266, 268, 270, 272, 274 when the seal assembly 260 is in the folded configuration (FIG. 14).

As shown, the ring portion 262a and the seal portion 262b of the support member 262 are of unitary construction, i.e., monolithic, with the first, second, third, fourth, fifth, and sixth seal sections 264, 266, 268, 270, 272, 274. By incorporating the ring portion 262a with the seal portion 262b of the support member 262 of the seal assembly 260 and forming the first, second, third, fourth, fifth, and sixth seal sections 264, 266, 268, 270, 272, 274 on the ring portion 262a of the support member 262, instead of including a ring portion for the seal portion and a separate ring portion for the first, second, third, fourth, fifth, and sixth seal sections 264, 266, 268, 270, 272, 274, the number of components in the seal assembly 260, and ultimately, the valve assembly 120, is reduced (FIG. 3). The incorporation of the seal portion 262b and the first, second, third, fourth, fifth, and sixth seal sections 264, 266, 268, 270, 272, 274 with the same ring portion 262 also reduces assembly time and reduces material costs.

Figure 12:
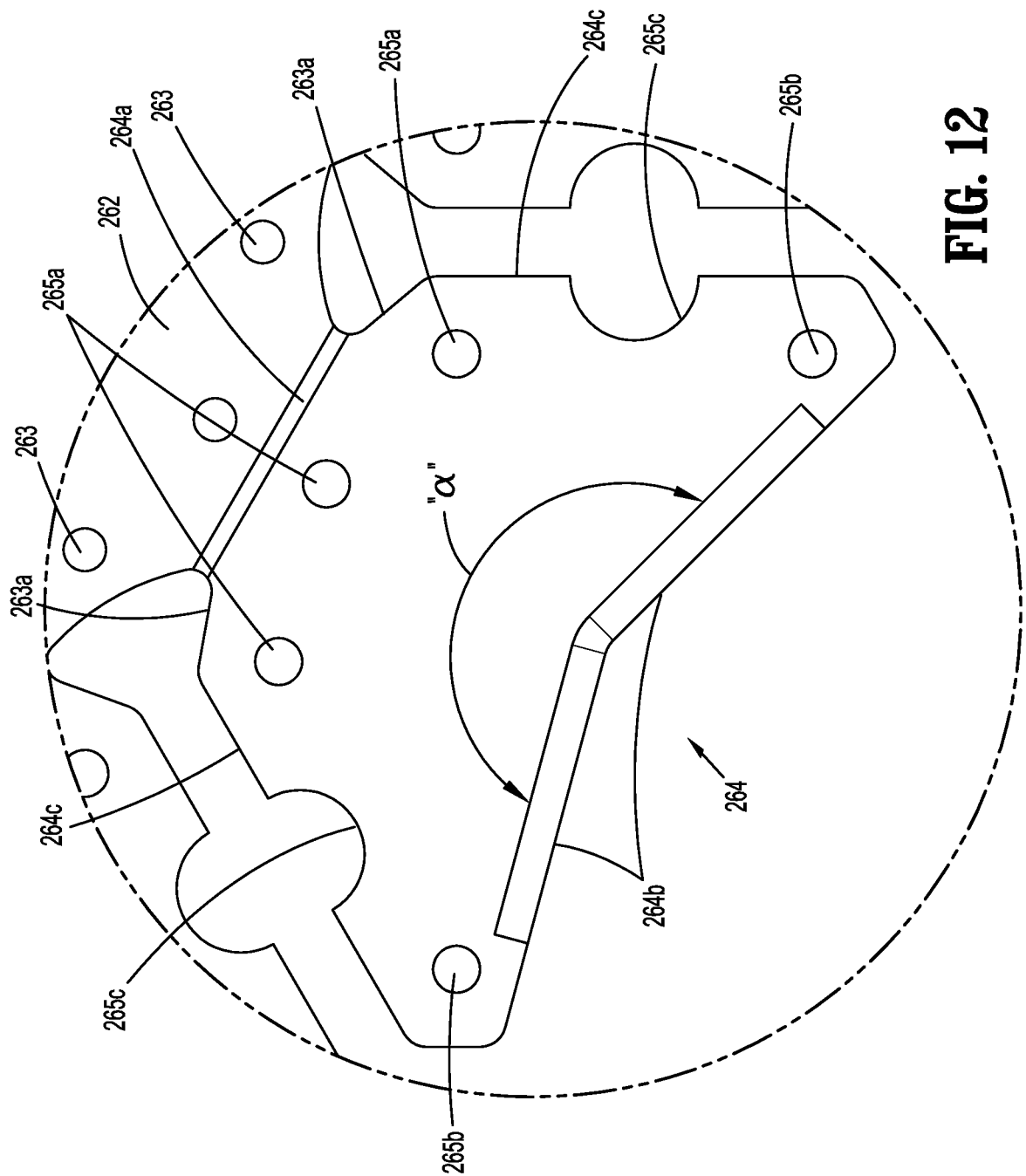
FIG. 12 is an enlarged view of the indicated area of detail shown in FIG. 11.

The first, second, third, fourth, fifth, and sixth seal sections 264, 266, 268, 270, 272, 274 of the seal assembly 260 are identical to each other in structure and function, and will be described in detail with reference to first seal section 264 shown in FIG. 12. The first seal section 264 includes a wing-shaped body secured to the support member 262 by a connector portion 264a. The connector portion 264a may include a single living hinge, as shown, or a plurality of living hinges (FIG. 4), or may be otherwise configured to permit folding of the first seal section 264 relative to the support member 262. The first seal section 264 and the support member 262 may define a notch 263a on either side of the connector portion 264a to facilitate folding of the first seal section 264 relative to the support member 262. The notches 263a may include a triangular configuration, as shown, or may be otherwise configured to facilitate folding of the first seal section 264 relative to the support member 262.

Inner edge 264b of the first seal section 264 of the seal assembly 260 may define a V-shape, as shown, or may extend straight across. In embodiments, the V-shape defines an angle "a" from about one-hundred eighty degrees (180°) to about two-hundred seventy-five degrees (275°). The V-shape of the inner edge 264b facilitates reception of a surgical instrument (not shown) through the seal assembly 260. Each inner edge 264b may be tapered to further facilitate reception of the surgical instrument through the seal assembly 260 in a sealed manner.

The first seal section 264 defines a plurality of openings 265a adjacent the connector portion 264a between the first seal section 264 and the support member 262, and an opening 265b along each lateral edge 264c of the first seal section 264 adjacent the inner edge 264b of the first seal section 264. The lateral edges 264c of the first seal section 264 each defines a semi-circular cutout 265c between each of the openings 265b and the plurality of openings 265a. The cutouts 265c reduce the amount of material forming the first seal section 264. The cutouts 265c may allow for additional flexing of the first seal section 264.

Figure 13:
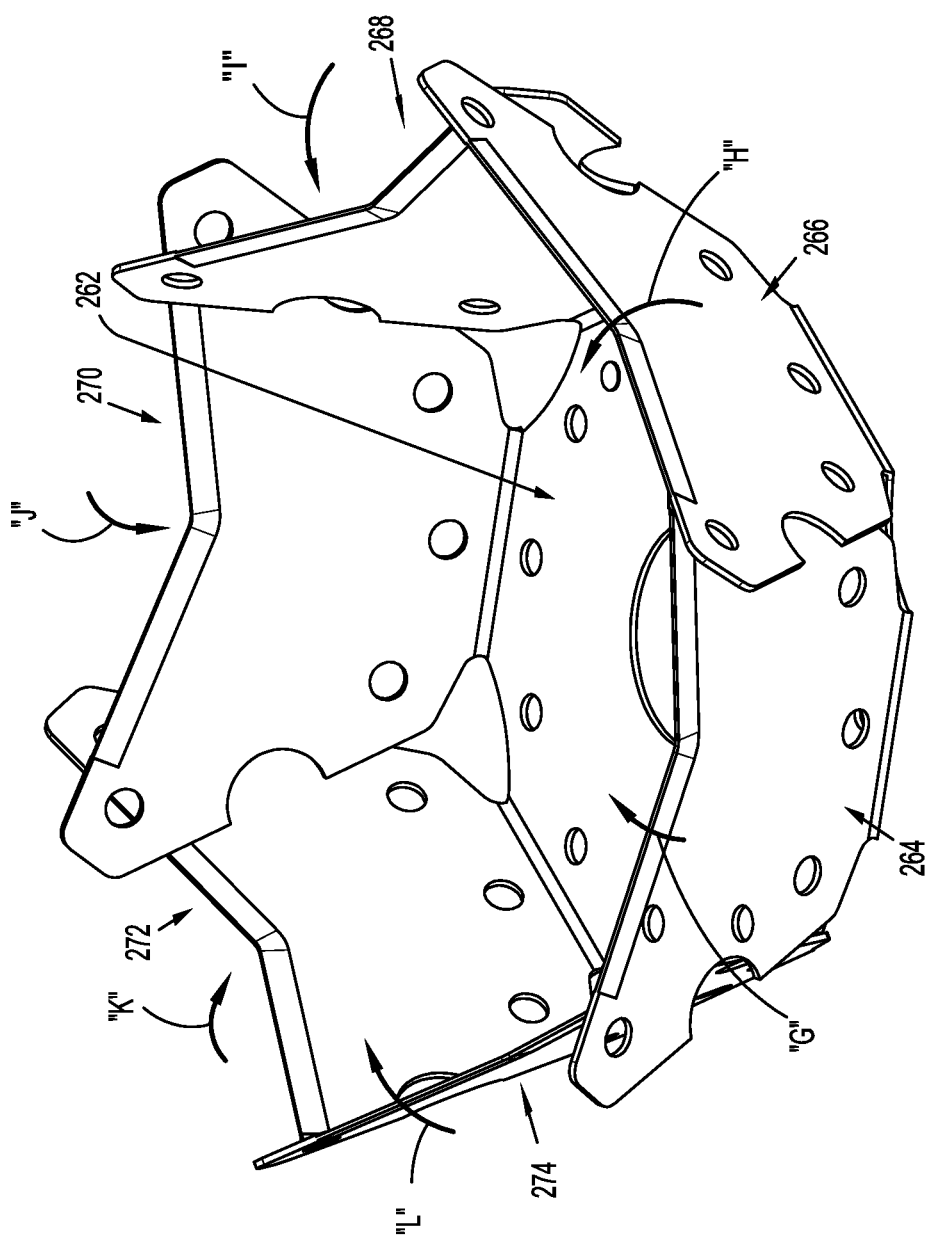
FIG. 13 is top perspective view of the seal assembly shown in FIGS. 10 and 11, in a partially folded condition.

FIG. 13 illustrates the method of folding the seal assembly 260. Each of the first, second, third, fourth, fifth, and sixth seal sections 264, 266, 268, 270, 272, 274 is folded relative to the support member 262, as indicated by arrows "G", "H", "I", "J", "K", and "L" respectively. As shown, the first, second, third, fourth, fifth, and sixth seal sections 264, 266, 268, 270, 272, 274 are folded simultaneously, with adjacent seal sections overlapping one another. More particularly, the second seal section 266, overlaps the first seal section 264, the third seal section 268 overlaps the second seal section 266, and so on until the first seal section 264 overlaps the sixth seal section 274. This overlapping or interweaving pattern increases the integrity of the seal assembly 260, i.e., reduces the likelihood of the seal assembly 260 leaking when a surgical instrument is received therethrough. As noted above, alternatively, the seal sections may be folded in any manner, including, with opposed seal sections folded together.

In some aspects of the disclosure, and as shown, the plurality of openings 265a and the openings 265b of the first seal section 264 are arranged such that, when the seal assembly 260 is in the folded condition (FIG. 14), each opening of the plurality of openings 263 in the support member 262 is aligned with an opening of the plurality of openings 265a of the first seal section 264, with two openings of each of the adjacent second and sixth seal sections 266 274, and with one opening of each of the third and fifth seal sections 268, 272. This arrangement ensures the integrity of the seal assembly 260, and more particularly, ensures the positioning of the first, second, third, fifth, and sixth seal sections 264, 266, 268, 2172, 274 relative to each other and the support member 262.

FIG. 14 illustrates the seal assembly 260 in the folded condition. In the folded condition, the first, second, third, fourth, fifth, and sixth seal sections 264, 266, 268, 270, 272, 274 of the seal assembly 260 define an opening 261a configured to receive a surgical instrument (not shown) inserted through the valve assembly 120 in a sealed manner. The first, second, third, fourth, fifth, and sixth seal sections 264, 266, 268, 270, 272, 274 form a non-continuous or virtual seal circumference to reduce tearing during insertion, manipulation, and/or withdrawal of a surgical instrument (not shown) through the valve assembly 120 (FIG. 3).

When the seal assembly 260 is in the folded configuration, the first, second, third, fourth, fifth, and sixth seal sections 264, 266, 268, 270, 272, 274 are configured to partially overlap two adjacent seal sections in each of the clockwise and the counter-clockwise directions. More particularly, the first seal section 264 is configured to partially overlap, the sixth and fifth seal sections 274, 272 in the clockwise direction and the second and third seal section 266, 268 in the counter-clockwise direction, the second seal section 264 is configured to partially overlap the first and sixth seal sections 264, 274 in the clockwise direction and the third and fourth seal sections 264, 268 in the counter-clockwise direction, the third seal section 266 is configured to partially overlap the second and first seal sections 266, 264 in the clockwise direction and the fourth and fifth seal section 270, 272 in the counter-clockwise direction, the fourth seal section 270 is configured to partially overlap the third and second seal sections 268, 266 in the clockwise direction and the fifth and sixth seal sections 272, 274 in the counter-clockwise direction, the fifth seal section 272 is configured to partially overlap the fourth and third seal sections 270, 268 in the clockwise direction and the sixth and first seal sections 274, 264 in the counter-clockwise direction, and the sixth seal section 274 is configured to partially overlap the fifth and fourth seal sections 272, 270 in the clockwise direction and the first and second seal sections 264, 266 in the counter clockwise direction.

In some aspects of the disclosure, and as shown, the first, second, third, fourth, fifth, and sixth seal sections 264, 266, 268, 270, 272, 274 are folded such that the first, second, third, fourth, fifth, and sixth seal sections 264, 266, 268, 270, 272, 274 overlap in a sequential pattern in counter-clockwise direction. Alternatively, the first, second, third, fourth, fifth, and sixth seal sections 264, 266, 268, 270, 272, 274 may folded to overlap in a sequential clockwise direction. It is envisioned that the first, second, third, fourth, fifth, and sixth seal sections 264, 266, 268, 270, 272, 274 may instead be folded in opposed pairs, i.e., first and fourth seal sections 264, 270 folded together, second and fifth seal sections, 266, 272 folded together, and third and sixth seal sections 268, 274 folded together, or in any other suitable manner.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the present disclosure be limited only by the spirit and scope of the appended claims.

What is claimed is:

1. An access assembly comprising:
   an instrument valve housing including upper, lower, and inner housing sections and defining a cavity; and
   a valve assembly disposed within the cavity of the instrument valve housing, the valve assembly including:
      a guard assembly; and
      a seal assembly disposed distal of the guard assembly, the seal assembly including a support member and a plurality of seal sections connected to the support member, the support member including a ring portion and a seal portion extending inward from and disposed within the ring portion, wherein the support member and the plurality of seal sections are integrally formed.

2. The access assembly of claim 1, wherein the plurality of seal sections of the seal assembly includes first, second, third, fourth, fifth, and sixth seal sections.

3. The access assembly of claim 1, wherein the ring portion is hexagonal.

4. The access assembly of claim 3, wherein each seal section of the plurality of seal sections includes a substantially wing shape.

5. The access assembly of claim 1, wherein an inner edge of each seal section of the plurality of seal sections is tapered.

6. The access assembly of claim 1, wherein each seal section of the plurality of seal sections is connected to the ring portion by a living hinge.

7. The access assembly of claim 1, wherein each seal section of the plurality of seal sections overlaps two adjacent seal sections of the plurality of seal sections in a clockwise direction.

8. The access assembly of claim 7, wherein each seal section of the plurality of seal sections overlaps two adjacent seal sections of the plurality of seal sections in a counter-clockwise direction.

9. The access assembly of claim 1, further including a retainer assembly including an upper retainer member, a lower retainer member, and a plurality of pins extending from one of the upper or lower retainer members.

10. The access assembly of claim 9, wherein each pin of the plurality of pins is received through an opening in three seal sections of the plurality of seal sections and through an opening in the ring portion of the support member.

11. A valve assembly comprising:
   a guard assembly; and
   a seal assembly disposed distal of the guard assembly, the seal assembly including a support member and a plurality of seal sections connected to the support member, the support member including a ring portion and a seal portion extending inward from and disposed within the ring portion, wherein the support member and the plurality of seal sections are integrally formed.

12. The valve assembly of claim 11, wherein the plurality of seal sections of the seal assembly includes first, second, third, fourth, fifth, and sixth seal sections.

13. The valve assembly of claim 11, wherein the ring portion is hexagonal.

14. The valve assembly of claim 13, wherein each seal section of the plurality of seal sections includes a substantially wing shape.

15. The valve assembly of claim 11, wherein an inner edge of each seal section of the plurality of seal sections is tapered.

16. The valve assembly of claim 11, wherein each seal section of the plurality of seal sections is connected to the ring portion by a living hinge.

17. The valve assembly of claim 11, wherein each seal section of the plurality of seal sections overlaps two adjacent seal sections of the plurality of seal sections in a clockwise direction and each seal section of the plurality of seal sections overlaps two adjacent seal sections of the plurality of seal sections in a counter-clockwise direction.

18. The valve assembly of claim 11, further including a retainer assembly including an upper retainer member, a lower retainer member, and a plurality of pins extending from one of the upper and lower retainer members.

19. The valve assembly of claim 18, wherein each pin of the plurality of pins is received through an opening in three seal sections of the plurality of seal sections and through an opening in the ring portion of the support member.

20. A seal assembly comprising:
a support member including a ring portion and a seal portion extending inward from and disposed within the ring portion; and
a plurality of seal sections extending from the ring portion of the support member, wherein the support member and the plurality of seal sections are integrally formed.

* * * * *